United States Patent [19]

Ribi

[11] Patent Number: 4,866,034
[45] Date of Patent: * Sep. 12, 1989

[54] REFINED DETOXIFIED ENDOTOXIN

[75] Inventor: Edgar E. Ribi, Hamilton, Mont.

[73] Assignee: Ribi Immunochem Research Inc., Hamilton, Mont.

[*] Notice: The portion of the term of this patent subsequent to Mar. 6, 2001 has been disclaimed.

[21] Appl. No.: 732,889

[22] Filed: May 8, 1985

Related U.S. Application Data

[63] Continuation of Ser. No. 526,967, Aug. 26, 1983, abandoned, which is a continuation-in-part of Ser. No. 382,404, May 26, 1982, Pat. No. 4,436,727.

[51] Int. Cl.$^4$ .................. A61K 37/02; A61K 37/00
[52] U.S. Cl. ............................. 514/2; 514/8; 424/88; 424/92; 435/68; 530/350; 530/351; 530/352; 530/359; 530/407; 530/806; 530/423; 530/825

[58] Field of Search ............... 514/2, 8; 424/85, 88, 424/92; 435/68; 530/352, 350, 359, 351, 403, 820, 407, 806, 825

[56] References Cited

U.S. PATENT DOCUMENTS

| | | | |
|---|---|---|---|
| 4,435,386 | 3/1984 | Ribi et al. | 514/2 |
| 4,436,727 | 3/1984 | Ribi | 514/2 |
| 4,436,728 | 3/1984 | Ribi et al. | 514/2 |
| 4,505,899 | 3/1985 | Ribi et al. | 514/8 |
| 4,505,900 | 3/1985 | Ribi et al. | 514/2 |
| 4,629,722 | 12/1986 | Ribi | 514/2 |

Primary Examiner—Robin Teskin
Attorney, Agent, or Firm—Burgess Ryan & Wayne

[57] ABSTRACT

A method is provided for producing an effective adjuvant response or stimulating the immune response of a warm blooded animal which comprises administering to said warm blooded animal an effective amount of a composition comprising refined detoxified endotoxin in combination with a pharmaceutically acceptable carrier.

20 Claims, No Drawings

REFINED DETOXIFIED ENDOTOXIN

This application is a continuation of Ser. No. 526,967, now abandoned, which is a continuation-in-part of Ser. No. 382,404, filed May 26, 1982, now U.S. Pat. No. 4,436,727.

BACKGROUND OF THE INVENTION

The present invention is directed to the use of a refined detoxified endotoxin (RDE) product as a potent immunostimulator and also as an adjuvant. The RDE used in the present invention is characterized as having no detectable 2-keto-3-deoxyoctanoate, between about 350 and 475 nmoles/mg of phosphorus and between about 1700 and 2000 nmoles/mg of fatty acids. Reference is made to U.S. Pat. No. 4,436,727 which describes the RDE product in detail including the method of preparation and which is incorporated herein.

Endotoxic extracts obtained from Enterobacteriaciae including parent organisms and mutants are known. These extracts have been used for immunotherapy of various immunogenic tumors [see *Peptides as Requirement for Immunotherapy of the Guinea-Pig Line-10 Tumor with Endotoxins;* Ribi, et al. Cancer Immunol. Immunother., Vol. 7, pgs. 43–58 (1979) incorporated herein by reference]. However, the endotoxin extracts are known to be highly toxic and, therefore, of limited use in the treatment of cancerous tumors. Efforts have been made to "detoxify" the endotoxins while retaining its tumor regressive capacity. As shown, in Ribi, et al., supra, chemical procedures known to "detoxify" endotoxins while retaining adjuvanticity, such as succinylation and phthalylation resulted in both loss of endotoxicity and tumor regressive potency. Therefore, prior art attempts to obtain a refined detoxified endotoxin product have thus far not been successful.

Endotoxin extracts of the type used as a starting material to produce the RDE used in the present invention may be obtained from any Enterobacteriaciae including parent organisms and mutants. By way of example, the following genera are illustrative of the type of microorganisms that may be used:

Salmonella, Shigella, Escherichia, Brucella, Bordetella, Citrobacter, Pseudomonas, Pasturella, Neisseria, Proteus, Klebsiella, and Serratia.

The following species are typically employed:

*S. minnesota, S. typhimuium, B. pertussis, B. abortus, S.enteritidis, E. coli, S. typhi, S. marcescens, S. typhosa, Shigella flexni,* and *S. abortus equi.*

The endotoxic extracts used as a starting material may be prepared by one of several known methods [see, for example, Webster, M. E., Sagin, J. F., Landy, M., and Johnson, A. G., *J. Immunol.* 1955, 744, 55; Westphal, O., Luderitz, O., and Bister, F., *Z. Naturforsch,* 76 148 (1952); Westphal. O., Pyrogens, *Polysaccharides in Biology, Tr. Second Macy Conference* (George F. Springer, ed.), Madison, N.J. Madison Printing Co., 1957, 115; Galanos, C., Luderitz, O., Westphal, O., *Eur. J. Biochem.* 9, 245 (1969); Chen, C. H., Johnson, A. G., Kasai, N., Key, B. A., Levin, J., Nowotny, A., *J. Infect. Dis.* 128 543 (1973); Ribi, E., Haskins, W.T., Landy, M., Milner, K. C., *The Journal of Experimental Medicine* 114 647 (1961); Leive, L., *Biochem. Biophys. Res. Comm.* 21 290 (1965); and Ribi, E., Milner, K. C., and Perrine, T., *J. Immunol.* 82 75 (1959)].

A most suitable method of obtaining the endotoxic extract is that disclosed by Chen, et al.; namely, methanol-chloroform precipitation.

The methanol-chloroform precipitate (MCP) is reacted with an organic or inorganic acid and then lyophilized to produce a hydrolyzed crude lipid A with reduced toxicity and pyrogenicity as compared with the starting endotoxin material. The resulting product is then treated with a solvent which is capable of specifically dissolving fatty acids and other impurities without dissolving the crude lipid A. A suitable solvent for this purpose is acetone. The phosphate content of the detoxified, refined lipid A is about one-half that observed for the toxic counterpart suggesting that the phosphate content is related to the toxic effects of endotoxins.

Suitable inorganic acids used to react with MCP are hydrochloric acid, sulfuric acid or phosphoric acid and the suitable organic acids are toluene sulfonic acid or trichloroacetic acid. The reaction may be suitably conducted at a temperature between about 90° and 130° C. for a time sufficient to complete hydrolysis usually between about 15 and 60 minutes.

The preparation of crude detoxified endotoxin may also be accomplished by reacting the starting material with the selected acid in the presence of an organic solvent such as chloroform, methanol, and ethanol or combinations thereof.

The resulting crude lipid A is dissolved in acetone which is particularly suited to remove the fatty acid components. The solvent is then removed to produce crude detoxified endotoxin.

The crude detoxified endotoxin is then dissolved in a solvent and passed through a suitable chromatographic column such as, for example, a molecular exclusion chromatographic column, to separate the RDE fractions which are then combined after removal of the solvent. In one embodiment, the crude detoxified endotoxin solution is passed through a Sephadex column in the presence of a solvent such as chloroform, methanol, acetone, pyridine, ether or acetic acid or combinations thereof. The pressure of the column may vary but is typically in the range of between about atmospheric and 100 lbs/in$^2$ and the flow rate is between about 0.1 and 10 ml/min.

Alternatively, the crude detoxified endotoxin solution is passed through a DEAE-cellulose column under the same pressure conditions as mentioned above for the Sephadex column. The flow rate may be maintained between about 2 and 15 ml/min. The solvents used are also the same as used for the Sephadex column although water and/or diethylamine can be added to all mixtures at a concentration of up to about 1%.

Other methods of producing RDE from crude detoxified endotoxin include passing the solution through a low pressure silica-gel 60 column having a particle size of between about 15 and 63 microns and using a suitable solvent such as chloroform, methanol, water or ammonium hydroxide. The preferred volume ratio of the aforementioned solvent mixture is about 50:25:4:2.

It is, therefore, an object of the present invention to employ a refined detoxified endotoxin product which can be effectively used to stimulate the immune system of a warm blooded animal. Specifically, RDE can be used as a B-cell mitogen, to stimulate the production of lymphokines, stimulate macrophages, and as an adjuvant which enhances the immune response of a warm blooded animal.

SUMMARY OF THE INVENTION

The present invention is directed to the use of refined detoxified endotoxin (RDE) as a stimulant of the immune system. The RDE used in this invention has no detectable 2-keto-3-deoxyoctanoate, between about 350 and 475 nmoles/mg of phosphorus and between about 1700 and 2000 nmoles/mg of fatty acids.

The RDE of the present invention can be used as a stimulant of the immune response in warm blooded aminals against antigens such as microbacterial and fungal cells, microbacterial cell fragments, viruses, virus sub units synthetic peptides which mimic cellular and viral sub units. Specific antigens which are affected by the immune response augmented by the administration of RDE include cryptococcus neoformans candida spp., *chlamydia* spp., *legionella* spp. *clostridia, hepatitis meningitis, streptococus* spp, pi staphylococus spp., *clebsiella* spp., *herpes virus, brucella* spp., *borditella* spp., *salmonella* spp., *shigella* spp., *camphylobacter* spp, *yersinia* spp., *pasturella* spp., *francisella* spp., *listeria* spp., and the like.

The RDE used in the present invention exhibits B-cell mitogenicity that is, RDE when administered to a warm blooded animal under a suitable dosage regimen activates B-lymphocytes which are the cells responsible for the manufacture of antibodies.

ASSAYS (1) B CELL MITOGENICITY—RDE is characterized by its ability to activate B lymphocytes which are the cells responsible for the manufacture of antibodies, as follows:

| MITOGENIC ACTIVITY OF REFINED DETOXIFIED ENDOTOXIN | | | |
|---|---|---|---|
| | Dose | $^3$H—thymidine incorporation | |
| | (μg/ml) | CPM* | SI** |
| BALB/c nu/+ | 10 | 34,500 | 5.0 |
| BALB/c nu/nu | 10 | 38,693 | 5.6 |

Protocol-
1 × 10$^6$ cells/ml of each strain cultured with or without mitogens in 0.2 mg of RPMI-1640 (5% FCS) in 96 well microtiter plates. 1 μcl $^3$H—Thymidine was added to each well the last 18 hours of a 48-hour incubation and $^3$H-incorporation was measured by standard scintillation techniques
*CPM - counts per minute
**SI - stimulation index (2) INTERLEUKIN I PRODUCTION The RDE can be used to stimulate the production of lymphokines released by macrophages. Interleukin-I is a soluble immunoregulator released by macrophages which is responsible for the activation of lymphocytes at the site of an infection. Interleukin-I plays a critical role as an amplifier of the immune response.

Murine macrphages are adhered to microtiter plates (1×10$^6$/well), each determination was made in triplicate. The first wells received 1 ml. of a 50 μg/ml solution of standard endotoxin produced in accordance with the procedure described in the aforesaid co-pending application, 1 ml. of a 50μg/ml solution of RDE in accordance with the present invention was added to the second set of wells. Each agent was solubilized in M 199 medium with 5% FCS (fetal calf serum). 1 ml. M 199 medium with 5% FCS was added to the third set of wells to serve as a control.

The plates were incubated at 37° C. for 20 hours. The supernatant was removed and diluted to obtain a solution having a 1:10 ratio of supernatant to distilled water. The supernatant was tested for interleukin-I production by the method of Gery, et al. *Cellular Immun.* 64, 293 (1981).

The cells remaining after removal of the supernatant were lysed using 0.1% Triton X - 100. The resulting solution was diluted with RPMI 1640 medium with 5% fetal calf serum at a 1:10 dilution ratio.

The diluted solution was tested for Interleukin-I production by measuring an augmentation of PHA inducted macrophage uptake of H$^3$-thymidine as described in Gery et al. supra. The results are shown in Table I.

TABLE I

| Test Material (50 μg/ml) | Supernatant Response (1:10 Dilution) | Lysate Response (1:10 Dilution) |
|---|---|---|
| Endotoxin Standard | 31,137 ± 1,721 | 51,695 ± 2797 |
| RDE | 16,782 ± 1,295 | 66,178 ± 2332 |
| Control | 3,323 ± 31 | 12,153 ± 497 |

As shown in Table I, Interleukin-I production from RDE of the present invention in the lysed cells greatly exceeded the Interleukin-I production from the standard endotoxin extract.

The same assay was conducted using human monocytes instead of murine macrophages.

The results are as follows:

TABLE IA

| Test Material (10 μg/ml.) | Supernatant Response (1:50 Dilution) | Lysate Response (1:50 Dilution) |
|---|---|---|
| Endotoxin Standard | 42,418 ± 1763 | 51,821 ± 1348 |
| RDE | 17,910 ± 1983 | 50,626 ± 813 |
| Control | 1,693 ± 289 | 15,173 ± 1,292 |

(3) MACROPHAGE ACTIVATION

RDE of the present invention also stimulates macrophages as measured by the ability of macrophages to phagocytize (engulf) fluorescent beads.

1×10$^6$ peritoneal exudate cells were mixed with 5 μl of a solution of a test material containing standard endotoxin, RDE of the present invention and saline as a control to respectively form three test solutions. Each of the solutions contained 1 μg of the test material and 20 μl of a fluorescent bead suspension. The test solutions were placed on individual microscope slides and then incubated for 90 minutes at 37° C.

After incubation, the slides were observed under a fluorescent microscope. By visual observation, the number of cells which phagocytosed the fluorescent beads were determined as well as the number of beads/cell.

The phagocytic index was calculated in accordance with the formula:

$$\text{PHAGOCYTIC INDEX} = \frac{\% \text{ cells phagocytosing} \times \text{number of beads}/100 \text{ cells}}{1000}$$

and the results of two experiments are shown in Table II.

TABLE II

|  | Phagocytic Index* | |
| --- | --- | --- |
|  | Expt. 1 | Expt. 2 |
| Endotoxin Standard | 5.0 | 3.6 |
| RDE | 5.4 | 4.1 |
| Control | 1.0 | 0.5 |

As can be seen from Table II, the phagocytic index for RDE of the present invention was significantly greater than that of standard endotoxin, thereby establishing that RDE is an exceedingly potent stimulator of macrophages.

(4) ADJUVANT ACTIVITY

To further establish the use of RDE as a stimulator of the immune system of warm blooded animals, RDE was tested for adjuvanticity as determined by its ability to augment the immune response to sheep red blood cells (SRBC) by measuring the ability of antibodies to lyse the sheep red blood cells.

Three test materials were prepared. Each contained $1 \times 10^7$ amount of SRBC. Test material #2 further contained 20 mcgs. of standard endotoxin+SRBC while test material #3 contained 20 mcgs. of RDE in accordance with the present invention+SRBC.

Test materials were injected interperitoneally into strain BALB/C mice. After 4-5 days, the test animals were sacrificed and the spleens removed and ground in a tissue grinder. A standard cell suspension of each spleen was made using a haemocytometer and each of the above suspensions were placed on slides along with the target SRBC, media, and agar.

The slides were incubated for 2 hours at 37° C. and Guinea Pig sera was added as a complement source to each of the slides followed by incubation for 30 minutes at 37° C.

Thereafter, the slides were examined to determine the quantity of plaque forming cells, which are areas in which antibodies destroyed the SRBC cells with the aid of the complement found in the Guinea Pig sera.

The results are shown in Table III.

TABLE III

| Test Material | PFC/$2 \times 10^5$ Spleen Cells |
| --- | --- |
| SRBC | 88 |
| SRBC + Endotoxin Standard | 165 |
| SRBC + RDE | 219 |

As can be seen from Table III, the number of plaque forming cells resulting from the use of RDE compared with standard endotoxin wsa significantly higher which establishes that RDE is a potent adjuvant.

The RDE as used in the present invention may be administered in combination with a pharmaceutically acceptable medium such as saline or an oil-droplet emulsion. The aforesaid composition may be stabilized as, for example, by a lyophilization procedure and then reconstituted without loss of potency.

As described above, the composition for treatment of warm blooded animals and humans may be used in the form of an oil droplet emulsion. The amount of oil used is in the range of between about 0.5 and 3.0 percent by volume based on the total volume of the composition. It is preferred to use between about 0.75 and 1.5 percent by volume of the oil. Examples of suitable oils include light mineral oil, squalane, 7-n-hexyloctadecane, Conoco superoil and Drakeol 6 VR mineral oil (produced by the Pennreco Company, Bulter, Pa).

The homogenized oil containing mixture is then combined with a detergent which may optionally be dissolved in a saline solution prior to mixing. The amount of detergent is typically between about 0.02 and 0.20 percent by volume and preferably between about 0.10 and 0.20 percent by volume based on the total volume of the composition. Any common detergent material may be used including Tween-80, and Arlacel (produced by the Atlas Chemical Company).

The mixture resulting from the addition of detergent is then homogenized to form a suspension which has a high percentage of oil droplets coated with RDE as determined by observation under a microscope.

The amount of RDE in a single injection is between 5 and 500 µg, preferably between 10 and 100µg (per total body weight of a 70 kg human adult.

1-3 injections are administered over a period of about 2 months.

The RDE composition used in the present invention exhibits significantly less pyrogenic activity than a composition containing standard endotoxin as evidenced by the following example.

Three New Zealand strain rabbits, were injected (into an ear vein) with a composition containing standard endotoxin. The amount of standard endotoxin necessary to cause an increase in body temperature of at least 0.46° C. in 50% of the test population was determined over a period of 3 hours using a rectal thermometer.

Three other test rabbits were also injected with a composition containing RDE and the same pyrogenic activity test was made. The results are shown in the following Table IV.

TABLE IV

| | PYROGENICITY |
| --- | --- |
| Test Material | Rabbit Activity* (in µg l/kg) |
| Endotoxin Standard | 0.012 |
| RDE | 10 (i.e. no fever at highest dose = 10 µg) |

*The dose necessary to cause a febrile (fever) response of greater than 0.46° C. in 50% of a test population.

As shown in Table IV, standard endotoxin produced a fever response in 50% of the test animals at a dosage of 0.012 µg/kg. RDE however, did not produce a fever response at >10µg/kg, which is 850 times the dose level of the standard endotoxin.

What is claimed is:

1. A method of producing an adjuvant response or stimulating the immune response of a warm blooded animal comprising injecting into said warm blooded animal an effective amount of a composition comprising refined detoxified endotoxin obtained from microorganisms of the Family Enterobacteriaciae and having no detectable 2-keto-deoxyoctanoate, between about 350 and 475 n moles/mg of phosphorus and between about 1700 and 2000 n moles/mg of fatty acids, in combination with a pharmaceutically acceptable carrier.

2. The method of claim 1 wherein said effective amount is between about 5 and 500 µg/kg.

3. The method of claim 2 wherein said effective amount is between about 10 and 100µg/kg.

4. The method of claim 1 wherein said composition is in lyophilized form.

5. The method of claim 1 wherein said composition is an oil droplet emulsion.

6. The method of claim 1 wherein the immune response comprises the activation of B lymphocytes in said warm blooded animal.

7. The method of claim 6 wherein said effective amount is between about 5 and 500 micrograms per total animal weight.

8. The method of claim 7 wherein said effective amount is between about 10 and 100 micrograms per total animal weight.

9. The method of claim 6 wherein said composition is an oil droplet emulsion.

10. The method of claim 1 wherein the immune response comprises the production of lymphokines in said warm blooded animal.

11. The method of claim 10 wherein said effective amount is between about 5 and 500 micrograms per total animal weight.

12. The method of claim 11 wherein said effective amount is between about 10 and 100 micrograms per total animal weight.

13. The method of claim 10 wherein said composition is in lyophilized form.

14. The method of claim 10 wherein said composition is an oil droplet emulsion.

15. The method of claim 1 wherein the adjuvant response comprises stimulating the production of antibodies in said warm blooded animal.

16. The method of claim 15 wherein said effective amount is between about 5 and 500 micrograms per total animal weight.

17. The method of claim 16 wherein said effective amount is between about 10 and 100 micrograms per total animal weight.

18. The method of claim 15 wherein said composition is in lyophilized form.

19. The method of claim 15 wherein said composition is an oil droplet emulsion.

20. A method of producing an adjuvant response or stimulating the immune response of a warm blooded animal comprising injecting into said warm blooded animal an effective amount of a composition comprising refined detoxified endotoxin having no detectable 2-keto-deoxyoctanoate, between about 350 and 475 n moles/mg of phosphorus and between about 1700 and 2000 n moles/mg of fatty acids, in combination with a pharmaceutically acceptable carrier, said refined detoxified endotoxin having been prepared by the steps of:
(a) hydrolyzing an endotoxin extract obtained from microorganisms of the Family Enterobacteriaciae with an inorganic or organic acid;
(b) lyophilizing the hydrolyzed product to obtain crude lipid A;
(c) treating crude lipid A with a first solvent capable of dissolving fatty acids and impurities without dissolving said crude lipid A;
(d) dissolving the resulting insoluble product in a second solvent in which said crude lipid A is soluble; and
(e) passing the resulting solution through a chromatographic column to obtain the desired refined detoxified endotoxin.

* * * * *

UNITED STATES PATENT AND TRADEMARK OFFICE
CERTIFICATE OF CORRECTION

PATENT NO.     : 4,866,034
DATED          : September 12, 1989
INVENTOR(S)    : Edgar E. Ribi It is certified that error appears in the above-identified patent and that said Letters Patent is hereby corrected as shown below:

On the face page, left-hand column, please replace "[t]he portion of the term of this patent subsequent to Mar. 6, 2001 has been disclaimed" with -- [t]he portion of the term of this patent subsequent to May 26, 2002 has been disclaimed --.

Signed and Sealed this

Fifteenth Day of May, 2001

Attest:

NICHOLAS P. GODICI

Attesting Officer        Acting Director of the United States Patent and Trademark Office